United States Patent
Hoyme et al.

(10) Patent No.: US 11,214,534 B2
(45) Date of Patent: Jan. 4, 2022

(54) ACRYLIC ACID PURIFICATION VIA DIVIDING WALL COLUMNS

(71) Applicant: Eastman Chemical Company, Kingsport, TN (US)

(72) Inventors: Craig Alan Hoyme, Fall Branch, TN (US); Robert Scott Huss, Kingsport, TN (US); Joseph Jerome Puhr, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/471,233

(22) PCT Filed: Dec. 15, 2017

(86) PCT No.: PCT/US2017/066770
§ 371 (c)(1),
(2) Date: Jun. 19, 2019

(87) PCT Pub. No.: WO2018/118702
PCT Pub. Date: Jun. 28, 2018

(65) Prior Publication Data
US 2020/0385329 A1     Dec. 10, 2020

Related U.S. Application Data

(60) Provisional application No. 62/437,722, filed on Dec. 22, 2016.

(51) Int. Cl.
*C07C 51/44* (2006.01)
(52) U.S. Cl.
CPC .................... *C07C 51/44* (2013.01)

(58) Field of Classification Search
None
See application file for complete search history.

(56) References Cited

U.S. PATENT DOCUMENTS 3,859,175 A   1/1975   Ohrui et al.
4,031,135 A   6/1977   Engelbach et al.
(Continued)

FOREIGN PATENT DOCUMENTS

CN   101 367 720 A   2/2009
DE   33 02 525 A1    7/1984
(Continued)

OTHER PUBLICATIONS

Mostefa, Marie Le Page et al.; "Determination of the Solid-Liquid Phase Diagram of the Binary System Acrylic Acid + Propionic Acid"; Journal of Chemical & Engineering Data, vol. 57; 2012; pp. 1209-1212.
(Continued)

*Primary Examiner* — Amy C Bonaparte
(74) *Attorney, Agent, or Firm* — Tammye L. Taylor Polk; C. Stuart Everett

(57) ABSTRACT

The present disclosure relates to a process for producing high-purity acrylic acid using a dividing wall distillation column and in some instances using water as an entrainer and azeotroping agent. This disclosure provides a process for separating acrylic acid from recovered feed streams which comprise saturated organic acids including propionic acid. The resulting acrylic acid product is of sufficient purity to produce acrylate esters and high molecular weight acrylic acid polymers.

16 Claims, 2 Drawing Sheets

(56) References Cited

U.S. PATENT DOCUMENTS

| | | | |
|---|---|---|---|
| 4,040,913 | A | 8/1977 | Clovis et al. |
| 4,147,885 | A | 4/1979 | Shimizu et al. |
| 4,365,087 | A | 12/1982 | Kadowaki et al. |
| 5,504,247 | A | 4/1996 | Saxer et al. |
| 6,254,735 | B1 | 7/2001 | Watzenberger |
| 6,482,981 | B2 | 11/2002 | Ueno et al. |
| 7,612,231 | B2 | 11/2009 | Kang et al. |
| 8,308,913 | B2 | 11/2012 | Kang et al. |
| 8,440,859 | B2 | 5/2013 | Dubois |
| 8,658,823 | B2 | 2/2014 | Peterson et al. |
| 8,765,629 | B2 | 7/2014 | Norman et al. |
| 8,883,672 | B2 | 11/2014 | Norman et al. |
| 8,932,434 | B2 | 1/2015 | Lee et al. |
| 8,993,801 | B2 | 3/2015 | Boppana et al. |
| 9,156,768 | B2 | 10/2015 | Meier et al. |
| 9,193,661 | B2 | 11/2015 | Peterson et al. |
| 9,493,393 | B2 | 11/2016 | Schultz et al. |
| 9,504,934 | B2 | 11/2016 | Agrawal et al. |
| 2013/0118892 | A1 | 5/2013 | Meier et al. |
| 2013/0317254 | A1 | 11/2013 | Kotsianis et al. |
| 2015/0119612 | A1 | 4/2015 | Agrawal et al. |
| 2019/0071382 | A1 * | 3/2019 | Fauconet .............. C07C 51/487 |

FOREIGN PATENT DOCUMENTS

| | | |
|---|---|---|
| EP | 1 116 709 A1 | 7/2001 |
| JP | H04 187657 A | 7/1992 |
| JP | H04187657 * | 7/1992 |
| WO | WO 2013 155245 A2 | 1/2013 |
| WO | WO 2015 031182 A1 | 3/2015 |
| WO | WO-2017060583 A1 * | 4/2017 ............ C07C 51/46 |

OTHER PUBLICATIONS

Olson, James D. et al.; "Thermodynamics of Hydrogen-Bonding Mixtures. 5. GE, HE, and TSE and Zeotropy of Water + Acrylic Acid"; Ind. Eng. Chem. Res., vol. 47, No. 15; 2008; pp. 5127-5131.

Co-pending U.S. Appl. No. 16/471,214, filed Jun. 19, 2019; Craig Alan Hoyme, et al.

Notification of Transmittal of the International Search Report and the Written Opinion of the International Searching Authority, or the Declaration received in International Application No. PCT/US2017/066761 dated Mar. 5, 2018.

Notification of Transmittal of the International Search Report and the Written Opinion of the International Searching Authority, or the Declaration received in International Application No. PCT/US2017/066770 dated Mar. 6, 2018.

Bauer, William; "Acrylic Acid and Derivatives"; Kirk-Othmer Encyclopedia of Chemical Technology; 41 pages; Jun. 20, 2003; retrieved online through Wiley Online Library, accessed Sep. 11, 2020 (https://onlinelibrary.wiley.com/doi/full/10.002/0471238961.0103182502012105.a01).

* cited by examiner

ACRYLIC ACID PURIFICATION VIA DIVIDING WALL COLUMNS

CROSS-REFERENCE TO RELATED APPLICATION(S)

This application is a national stage filing under 35 USC § 371 of International Application Number PCT/US2017/066770, filed on Dec. 15, 2017; which claims the benefit of the filing date to U.S. Provisional Application No. 62/437,722 filed on Dec. 22, 2016; the entire disclosures of which are incorporated by reference herein.

FIELD OF THE INVENTION

The present disclosure relates to a process for producing high-purity acrylic acid using a dividing wall distillation column and in some instances using water as an entrainer and azeotroping agent. More specifically, this disclosure relates to processes and apparatuses for using a dividing wall distillation column to separate acrylic acid from feeds comprising saturated organic acids. In some instances, this disclosure further relates to the use of a dividing wall distillation column with the azeotropic purification of acrylic acid from saturated organic acid streams comprising propionic acid using water as an entrainer and azeotroping agent.

BACKGROUND OF THE INVENTION

Purified acrylic acid (prop-2-enoic acid) is a necessary building block for the production of acrylate esters and superabsorbent polymers. Superabsorbent polymers are used in applications such as disposable diapers, ion exchange resins, adhesives, detergents, and thickening agents for pharmaceuticals, cosmetics, and paints. Very pure acrylic acid is necessary for the production of superabsorbent polymers. Reaction impurities must be separated from the acrylic acid to enable the production of these high molecular weight acrylic acid polymers.

During the production of acrylic acid, reaction by-products are formed that must be separated from the acrylic acid to enable the production of the acrylate esters and superabsorbent polymers. The purification process of acrylic acid to obtain glacial acrylic acid; typically, requires the separation of acrylic acid from mixtures comprising propionic acid and/or mixtures comprising acetic acid. The separation of propionic acid from acrylic acid is an especially difficult separation to accomplish because acrylic acid and propionic acid are close boiling in nature and form a minimum boiling homogeneous azeotrope (the boiling point of acrylic acid is 142.0° C., the boiling point of propionic acid is 140.9° C., the boiling point of the minimum boiling azeotrope is 140.2° C.). Unfortunately, propionic acid is a by-product found in most acrylic acid production processes including, but not limited to, propylene oxidation, the aldol condensation of formaldehyde and acetic acid, and the bio-based production of acrylic acid from glycerol.

The separation of acetic acid from acrylic acid is also necessary to produce high-purity acrylic acid. This separation may also be required for processes involving the production of acrylic acid from formaldehyde and acetic acid because any unreacted acetic acid must be recycled back to the reactor to ensure a high conversion of the acetic acid to the desired acrylic acid product. This present disclosure provides a process in which a chemical mixture comprising acrylic acid and propionic acid or acrylic acid and acetic acid are separated using a dividing wall distillation column to produce an acrylic acid product of sufficient purity to produce high molecular weight acrylic acid polymers.

SUMMARY OF THE INVENTION

One aspect of the present disclosure is a process for purifying acrylic acid from a feed stream composition comprising acrylic acid, water, and acetic acid using a dividing wall column, the process comprising:
supplying a feed stream into the dividing wall column operated at a temperature and pressure such that the feed stream is separated into at least a product top stream, a product bottom stream, and a product side stream and optionally a concentrated product upper side stream;
wherein the feed stream and the product side stream are located on opposite sides of the column and are separated by the dividing wall and wherein the dividing wall extends essentially vertically through the column from a dividing wall-free column top zone to a dividing wall-free column bottom zone, and
wherein the product top stream comprises water, acetic acid, and low boiling by-products, the product bottom stream comprises high-boiling by-products, and the product side stream comprises acrylic acid and the optional the concentrated product upper side stream near the top of the column comprises a concentrated acid side-stream comprising acetic acid, and wherein the optional concentrated product upper side stream is located above the dividing wall in the wall-free column top zone.

One aspect of the present disclosure is a process for purifying acrylic acid from a feed stream composition comprising acrylic acid, water, acetic acid, and propionic acid using a dividing wall column, the process comprising:
supplying a feed stream into the dividing wall column operated at a temperature and pressure such that the feed stream is separated into at least a product top stream, a product bottom stream, and a product side stream and optionally a concentrated product upper side stream;
wherein the feed stream and product side stream are located on opposite sides of the column and are separated by the dividing wall, and wherein the dividing wall extends essentially vertically through the column from a dividing wall-free column top zone to a dividing wall-free column bottom zone; and
adding water as an entrainer and azeotroping agent, into a dividing wall-free column top zone in the column,
wherein the product top stream comprises water, acetic acid, propionic acid and low boiling by-products, the product bottom stream comprises high-boiling by-products, and the product side stream comprises acrylic acid and optionally the concentrated product upper side stream near the top of the column comprises a concentrated acid side-stream comprising acetic acid, and wherein the optional concentrated upper side stream is located above the dividing wall in the wall-free column top zone.

One aspect of the present disclosure is a process for purifying acrylic acid from a feed stream composition comprising acrylic acid, water, and acetic acid using a dividing wall column, the process comprising:
supplying a feed stream into the dividing wall column operated at a temperature and pressure such that the feed stream is separated into product top streams (one on each side of the column), product bottom streams (one on each side of the column), and a product side stream (on one side of the column opposite the feed stream) and optionally concentrated product upper side streams (optionally one on either side of the column or both on one side of the column);

wherein the feed stream and product side stream are located on opposite sides of the column and are completely separated by the dividing wall and wherein the dividing wall extends vertically through the entire column from the top of the column to the bottom of the column; and optionally adding water as an entrainer and azeotroping agent (wherein the entrainer is fed into the top of the column on either side of the column), wherein the product top streams comprise water, acetic acid, and low boiling by-products, the product bottom streams comprise high boiling by-products, and the product side stream comprises acrylic acid and the optional concentrated product upper side stream near the top of the column comprises a concentrated acid side-stream comprising acetic acid.

One embodiment of the present disclosure is a process wherein the feed stream comprises 1-80 wt % acrylic acid, 0-80 wt % acetic acid, and 0-60 wt % additional components where the total composition does not exceed 100 wt % and wherein the product side stream is high purity acrylic acid with less than 500 ppm acetic acid.

One embodiment of the present disclosure is a process wherein the feed stream comprises 5-50 wt % acrylic acid, 50-80 wt % acetic acid, 1-20 wt % water, and 0.5-1 wt % propionic acid or wherein the feed stream comprises 50-80 wt % acrylic acid, 0.1-20 wt % acetic acid, 0.1-10 wt % water, and 0.001-0.5 wt % propionic acid and wherein the product side stream is high purity acrylic acid with less than 500 ppm acetic acid and less than 100 ppm propionic acid.

One embodiment of the present disclosure is a process wherein the feed stream comprises less than 80 wt % acrylic acid.

DETAILED DESCRIPTION OF THE INVENTION

Figure 1:
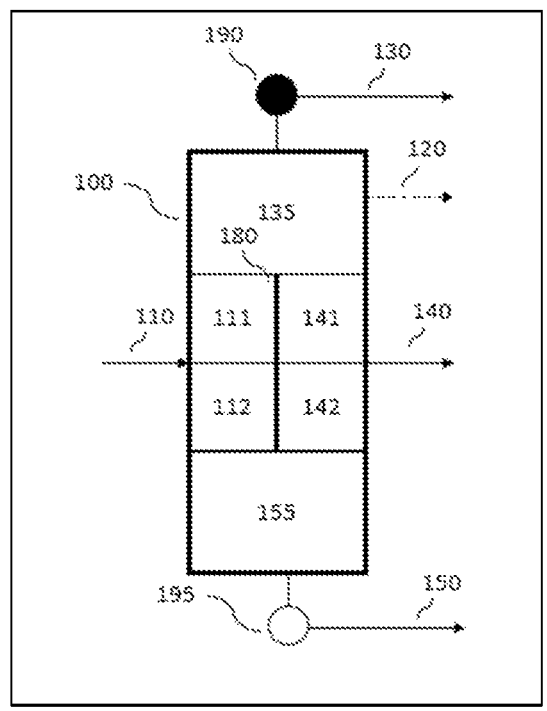
FIG. 1 illustrates a dividing wall column of the present invention.

The purification of acrylic acid from the initial production reaction by-products is an energy and capital intensive operation. To produce superabsorbent polymers, the acrylic acid product must meet stringent product specifications. Typically, for superabsorbent polymers, the total aldehydes must be less than 10 ppm, the total saturated acids must be less than 1600 ppm, acetic acid is less than 500-1500 ppm, and propionic acid is less than 100-500 ppm. To obtain these specifications, many separation steps are required, and they can include multiple unit operations such as distillation, extraction, and/or crystallization. Dividing wall columns have been found to reduce process energy and the capital required when compared to conventional distillation separation sequences. The use of dividing wall columns to separate and purify acrylic acid provides a more energy efficient and less capital-intensive process.

Acrylic acid suitable for use in the present disclosure can be produced from many different starting materials and routes. In one embodiment of the present disclosure, the production route of the acrylic acid is the oxidation of propylene to acrylic acid. In another embodiment, the production route of the acrylic acid is from the aldol condensation reaction of formaldehyde and acetic acid. In one embodiment, bio-based production routes of acrylic acid are also suitable in the present disclosure. These processes have some similar separation challenges, but also have unique separation issues that can result in a process that is both energy and capital intensive.

For example, during the aldol condensation reaction between formaldehyde and acetic acid, there is typically a measurable amount of unreacted acetic acid. Acetic acid can also be used in excess to improve the overall conversion of the formaldehyde and act as a diluent for acrylic acid in order to minimize the acrylic acid oligomerization inherent to its production. The efficient separation of acetic acid from acrylic acid and the subsequent recycle of the acetic acid is a necessary part of this process.

The purification of acrylic acid from mixtures comprising propionic acid is difficult using conventional distillation because acrylic acid and propionic acid are close boiling in nature and form a minimum boiling homogeneous azeotrope (the boiling point of acrylic acid is 142.0° C., the boiling point of propionic acid is 140.9° C., the boiling point of the minimum boiling azeotrope is 140.2° C.). Due to the formation of the minimum boiling azeotrope, it is not possible to completely separate propionic acid from acrylic acid and recover the vast majority of the desired acrylic acid product in a highly refined state using conventional distillation.

During the production of acrylic acid from acetic acid and formaldehyde, propionic acid and other components are produced at low, but not inconsequential concentrations. The purification of the desired acrylic acid generates an intermediate acrylic acid product stream comprising acrylic acid, propionic acid, acetic acid, and other reaction impurities. Using water as an entrainer in an azeotropic dividing wall distillation column will result in the separation of propionic acid and other components which form minimum boiling azeotropes with water from the desired acrylic acid product.

One aspect of the present disclosure, enables the separation of propionic acid from acrylic acid by using a dividing wall distillation column and using water as an entrainer and azeotroping agent. Water forms a minimum boiling azeotrope with propionic acid but does not form an azeotrope with acrylic acid. Thus, in one embodiment of the present disclosure, the addition of the appropriate amount of water to a dividing wall distillation column with a feed stream comprising acrylic acid and propionic acid enables the separation of propionic acid from the acrylic acid with the propionic acid and water as the column distillate top stream product and acrylic acid as the column side stream product.

One aspect of the present disclosure, enables the separation of acetic acid from acrylic acid by using a dividing wall distillation column. In these embodiments, the separation takes place without adding water as an entrainer and azeotroping agent.

One embodiment of the present invention is to remove propionic acid and other compounds from an intermediate acrylic acid product produced from the reaction of acetic acid and formaldehyde.

Another embodiment of the present invention is to remove propionic acid and other compounds from an acrylic acid stream.

Another embodiment of the present invention is to remove propionic acid and other compounds from a concentrated impurity purge stream produced during the purification of acrylic acid.

In one embodiment of the present disclosure, the dividing wall distillation column includes a main column having a vertical dividing wall. As shown in FIG. 1, in some embodiments, the dividing wall column may optionally have one or more condensers 190 and/or one or more reboilers 195. In some embodiments, the dividing wall column may have one or more condensers, and in some embodiments, the dividing wall column may have one or more reboilers. In some embodiments, the dividing wall column does not have condensers, and in some embodiments, the dividing wall column does not have reboilers. The main column 100 is divided into an upper feed zone 111, a lower feed zone 112, an upper outflow zone 141, a lower outflow zone 142, a column top zone 135, and a column bottom zone 155. The dividing wall column 100 has at least one feed stream 110 introduced to the dividing wall column between the upper feed zone 111 and the lower feed zone 112, a product top stream 130, a product bottom stream 150, a product side stream 140 that is removed between the upper outflow zone 141 and the lower outflow zone 142, and in some embodiments, there is optionally a concentrated product upper side stream 120. Accordingly, since one distillation column can be used to realize the same effect as that obtained from the use of two distillation columns, the dividing wall distillation column can have an effect of reducing the capital costs of the equipment to produce high-purity acrylic acid, as well as an energy-reducing effect, compared to a conventional process system.

In one embodiment, the feed zones 111, 112 and outflow zones 141, 142 are located on opposite sides of the column 100 and are separated by the dividing wall 180. In some embodiments, the dividing wall 180 extends essentially vertically through the column 100 from a dividing wall-free column top zone 135 to a dividing wall-free column bottom zone 155. In other embodiments, such as FIG. 4 discussed below, the feed stream 410 and product side stream 440 are located on opposite sides of the column and are completely separated by the dividing wall 480 and the dividing wall 480 extends vertically through the entire column from the top of the column to the bottom of the column.

Figure 2:
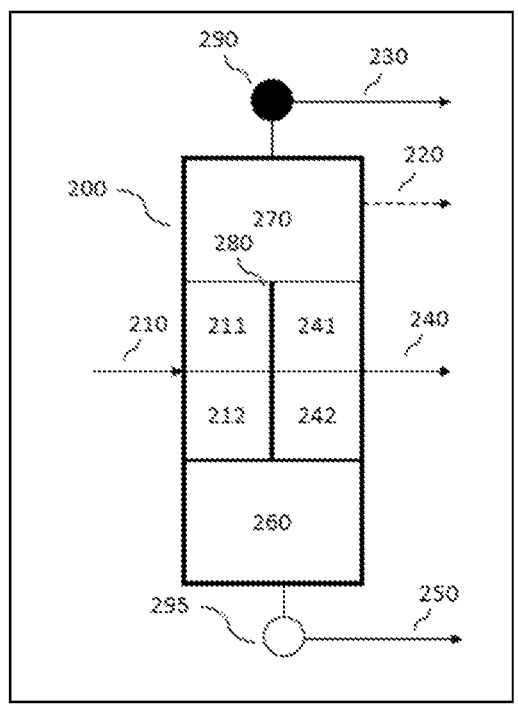
FIG. 2 illustrates a dividing wall column of the present invention.

One embodiment of the present invention, as shown in FIG. 2, is a process for purifying acrylic acid from a feed stream composition that comprises acrylic acid, water, and acetic acid using a dividing wall column 200, optionally, with one or more condensers 290 and/or one or more reboilers 295 where the main column 200 is divided into an upper feed zone 211, a lower feed zone 212, an upper outflow zone 241, a lower outflow zone 242. The process comprising: supplying a feed stream 210 into the dividing wall column operated at a temperature and pressure such that the feed stream is separated into at least a product top stream 230, a product bottom stream 250, and at least one product side stream 240 and in some embodiments these is optionally at least one concentrated product upper side stream 220, wherein the feed zones and outflow zones are located on opposite sides of the column and are separated by the dividing wall 280 and wherein the dividing wall extends essentially vertically through the column from a dividing wall-free column top zone 270 to a dividing wall-free column bottom zone 260, wherein the product top stream 230 comprises water, acetic acid, and low boiling by-products, the product bottom stream 250 comprises high-boiling by-products, and the product side stream 240 comprises acrylic acid and in some embodiments the optional concentrated product upper side stream 220 near the top of the column comprises a concentrated acid side stream comprising acetic acid, wherein the optional concentrated product upper side stream is located above the dividing wall in the wall-free column top zone.

In some embodiments, the feed stream comprises 1-80 wt % acrylic acid, 0-80 wt % acetic acid, and 0-60 wt % additional components where the total composition does not exceed 100 wt %. In some embodiments, the feed stream comprises 1-80 wt % acrylic acid, 1-80 wt % acetic acid, and 1-60 wt % additional components where the total composition does not exceed 100 wt %. In one embodiment, the feed stream comprises 5-25 wt % acrylic acid, 50-80 wt % acetic acid, 5-20 wt % water, and 0.001-0.3 wt % propionic acid. In one embodiment, the feed stream comprises 5-50 wt % acrylic acid, 50-80 wt % acetic acid, 0.1-20 wt % water, and 0.05-1 wt % propionic acid. In another embodiment, the feed stream comprises 50-80 wt % acrylic acid, 10-20 wt % acetic acid, 3-10 wt % water, and 0.001-0.3 wt % propionic acid. In another embodiment, the feed stream comprises 60-80 wt % acrylic acid, 0.01-5 wt % acetic acid, 0.01-5 wt % water, and 0.01-5 wt % propionic acid. In another embodiment, the feed stream comprises 50-80 wt % acrylic acid, 0.1-20 wt % acetic acid, 0.1-10 wt % water, and 0.001-0.5 wt % propionic acid. In some embodiments, the feed stream comprises less than 80 wt % acrylic acid. In some embodiments, the additional components comprise by-products from the initial reaction to produce acrylic acid and they may comprise high boiling, lower boiling or intermediate boiling components such as propionic acid, furfural, benzaldehyde, maleic acid, toluene, or other impurities. In one embodiment, the total amount of additional components is less than 5 wt %; particularly in embodiments when the feed stream is from an intermediate stream coming directly from the initial reaction to produce acrylic acid followed by some additional distillation steps. In other embodiments, the total amount of additional components can be much greater than 5 wt % when the feed stream comes from a distillation high-boiler purge or from a melt crystallization purge stream in which they are separated and concentrated from the acrylic acid in the intermediate stream.

In one embodiment, greater than 80 wt % of the acrylic acid in the feed is recovered in the product side stream. In another embodiment, greater than 85 wt % of the acrylic acid in the feed is recovered in the product side stream. In another embodiment, greater than 90 wt % of the acrylic acid in the feed is recovered in the product side stream. In another embodiment, greater than 92 wt % or greater than 93 wt % or greater than 94 wt % of the acrylic acid in the feed is recovered in the product side stream. In another embodiment, greater than 95 wt % of the acrylic acid in the feed is recovered in the product side stream. In another embodiment, greater than 99 wt % of the acrylic acid in the feed is recovered in the product side stream. In another embodiment, greater than 99.5 wt % of the acrylic acid in the feed is recovered in the product side stream. In another embodiment, greater than 99.7 wt % of the acrylic acid in the feed is recovered in the product side stream.

In one embodiment of the present disclosure, the dividing wall column may be operated at any suitable conditions for acrylic acid purification. In one embodiment, the column must be operated at temperatures, pressures and residence times to minimize the oligomerization of acrylic acid. In one embodiment of the present disclosure, the column temperature is controlled to temperatures of 115° C. to 150° C. where the acrylic acid concentration is greater than 35 wt %. In one embodiment, the column temperature is controlled to a temperature less than 115-150° C. where the acrylic acid concentration is greater than 35 wt %. In one embodiment of the present disclosure, the column temperature is controlled to less than 150° C. where the acrylic acid concentration is greater than 35 wt %. In one embodiment of the present disclosure, the column temperature is controlled to less than 140° C. where the acrylic acid concentration is greater than 35 wt %. In one embodiment of the present disclosure, the column temperature is controlled to less than 135° C. where the acrylic acid concentration is greater than 35 wt %. In another embodiment, the column temperature is controlled to less than 130° C. where the acrylic acid concentration is greater than 35 wt %. In one embodiment of the present disclosure, the column temperature is controlled to less than 125° C. where the acrylic acid concentration is greater than 35 wt %. In another embodiment, the column temperature is controlled to less than 120° C. where the acrylic acid concentration is greater than 35 wt %. In another embodiment, the column temperature is controlled to less than 115° C. where the acrylic acid concentration is greater than 35 wt %. In some embodiments, the column operates at a pressure less than or equal to 1000 torr.

In one embodiment, the azeotropic distillation operates at a pressure less than or equal to 1000 torr. In one embodiment, the azeotropic distillation operates at a maximum temperature from about 110° C. to about 150° C. or from about 120° C. to about 140° C. where the acrylic acid concentration is greater than 35 wt %; for example, at temperatures less than about 150° C., or at a temperature less than about 140° C., or at temperature less than about 130° C., or at a temperature less than about 120° C., or at a temperature less than about 115° C. where the acrylic acid concentration is greater than 35 wt %.

In one embodiment of the present disclosure, the product side stream comprises high purity acrylic acid. In some embodiments, the high purity acrylic acid comprises a total aldehydes concentration of less than 10 ppm, the total saturated acid concentration is less than 1600 ppm, the acetic acid concentration is less than 500-1500 ppm, and the propionic acid concentration is less than 100-500 ppm. In some embodiments, the high purity acrylic acid comprises an acetic acid concentration less than 500 ppm, and a propionic acid concentration less than 100 ppm. In some embodiments, the high purity acrylic acid comprises an acetic acid concentration less than 500 ppm.

In one embodiment, the feed stream comprises 1-80 wt % acrylic acid, 0-80 wt % acetic acid, and 0-60 wt % additional components where the total composition does not exceed 100 wt % and the product side stream is high purity acrylic acid with less than 500 ppm acetic acid. In another embodiment, the feed stream comprises 5-50 wt % acrylic acid, 50-80 wt % acetic acid, 1-20 wt % water, and 0.5-1 wt % propionic acid or the feed stream comprises 50-80 wt % acrylic acid, 0.1-20 wt % acetic acid, 0.1-10 wt % water, and 0.001-0.5 wt % propionic acid and the product side stream is high purity acrylic acid with less than 500 ppm acetic acid and less than 100 ppm propionic acid.

Figure 3:
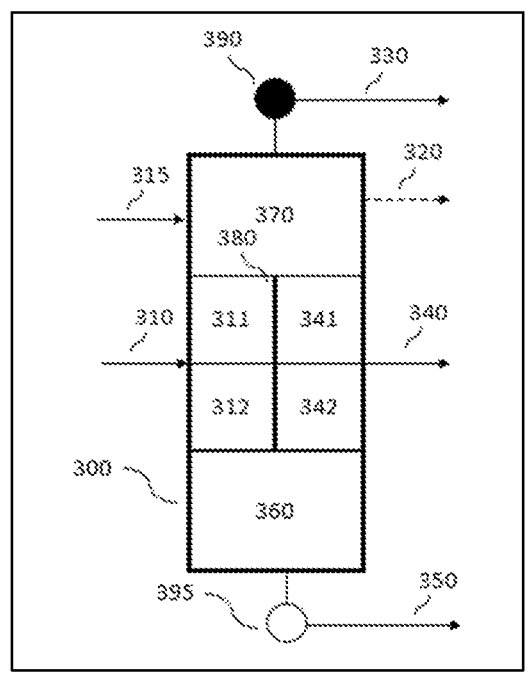
FIG. 3 illustrates a dividing wall column with the azeotropic distillation of acrylic acid.

Some embodiments of the present disclosure, as shown in FIG. 3, provide a process for purifying acrylic acid from a feed stream 310 composition that comprises water, acrylic acid, acetic acid, and propionic acid using a dividing wall column, in some embodiments, the column optionally has one or more condensers 390 and/or one or more reboilers 395, the process comprising: supplying a feed stream 310 into the dividing wall column 300 operated at a temperature and pressure such that the feed stream is separated into at least a product top stream 330, a product bottom stream 350, and a product side stream 340 and in some embodiments, optionally there is an upper concentrated product side stream 320, and adding an entrainer 315 consisting essentially of water into the column top zone 370 of the column, wherein the upper feed zone 311 and lower feed zone 312 are located on opposite sides of the column from the upper outflow zone 341 and lower outflow zone 342 and are separated by the dividing wall 380 and wherein the dividing wall extends essentially vertically through the column from a dividing wall-free column top zone 370 to a dividing wall-free column bottom zone 360, wherein the product top stream 330 comprises water, acetic acid, propionic acid and low boiling by-products, the product bottom stream 350 comprises high-boiling by-products, and the product side stream 340 comprises acrylic acid and the optional concentrated product upper side stream 320 near the top of the column comprises a concentrated acid side-stream comprising acetic acid, wherein the optional concentrated product upper side stream is located above the dividing wall 380 in the column top zone 370.

In one embodiment of the present disclosure, the amount of water added to the column may be any amount suitable to enable the water to act as an entrainer and azeotroping agent. The recovery of propionic acid, other C3+ saturated organic acids (C3+ means a saturated organic acid with 3 or more carbon atoms), and other organic compounds forming minimum boiling azeotropes with water is enabled by the use of water as an entrainer. Water forms minimum boiling azeotropes with C3+ saturated organic acids which are lower boiling than acrylic acid and lower boiling than any acrylic acid/C3+ saturated organic acid azeotropes. This enables water to remove the C3+ saturated organic acids in a distillation column as long as enough water is added to the column and if the column is operated under appropriate conditions. The amount of water required for the separation is typically determined by the feed composition, desired saturated organic acid recovery and column operation parameters such as distillate to feed ratio, reflux ratio, and other typically controlled column parameters. In one embodiment, the water to feed ratio (wt/wt) in the azeotropic distillation is greater than 1.0. In another embodiment, the water to feed ratio is greater than 1.2. In another embodiment, the water to feed ratio is greater than 1.3. In another embodiment, the water to feed ratio is greater than 1.4. In another embodiment, the water to feed ratio is greater than 1.5. In some embodiments, the water to feed ratio (wt/wt) in the azeotropic distillation is 1.5 to 4 or 1.5 to 3 or 1.5 to 2.

Figure 4:
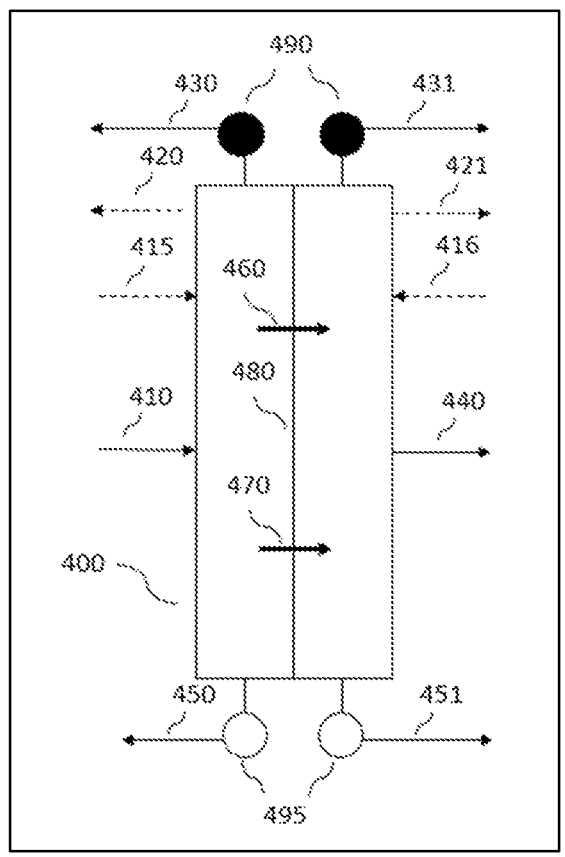
FIG. 4 illustrates a dividing wall column with a dividing wall that extends vertically through the entire length of the column from the top of the column to the bottom of the column.

Some embodiments of the present disclosure, as shown in FIG. 4, provide a process for purifying acrylic acid from a feed stream 410 composition that comprises acrylic acid, water, and acetic acid using a dividing wall column 400, optionally with one or more condensers 490 and/or one or more reboilers 495, the process comprising: supplying a feed stream 410 into the dividing wall column operated at a temperature and pressure such that the feed stream is separated into product top streams 430, 431 (one on each side of the column), product bottom streams 450, 451 (one on each side of the column), and a product side stream 440 (on one side of the column, opposite the feed stream) and in some embodiments, optionally there are concentrated upper side streams 420, 421 (optionally one on either side of the column or both on one side of the column), wherein the feed stream 410 and the product side stream 440 are located on opposite sides of the column and are completely separated by the dividing wall 480 and wherein the dividing wall extends vertically through the entire column from the top of the column to the bottom of the column with liquid transfers across the wall where a portion of the liquid is transferred from one side of the wall to the other side of the wall, and there is an upper liquid transfer stream 460 and a lower liquid transfer stream 470, and wherein the product top streams 430, 431 comprise water, acetic acid, and low boiling by-products, the product bottom streams 450, 451 comprise high boiling by-products, and the product side stream 440 comprises acrylic acid and the optional concentrated product upper side streams 420, 421 near the top of the column comprise a concentrated acid side-stream comprising acetic acid. In some embodiments, the feed stream 410 composition comprises water, acrylic acid, acetic acid, and propionic acid; in these embodiments, water can optionally be added as an entrainer 415 (in one embodiment, there is an entrainer feed 415, 416 on each side of the column above the upper liquid transfer stream 460), wherein the water acts as an entrainer and azeotroping agent. In these embodiments, the product top streams 430, 431 comprise water, acetic acid, propionic acid and low boiling by-products, the product bottom streams 450, 451 comprise high boiling by-products, and the product side stream 440 comprises acrylic acid and the optional concentrated product upper side streams 420, 421 near the top of the column comprises a concentrated acid side-stream comprising acetic acid. In these embodiments, the optional upper side stream is located above the liquid transfer stream 460.

In another aspect of the present disclosure, the feed stream is recovered from the production of acrylic acid by an aldolization reaction, said feed stream comprising acrylic acid, acetic acid, propionic acid, water, and high boiling by-products. For example, such processes are described in U.S. Pat. Nos. 8,765,629, and 8,883,672 which are herein incorporated by reference.

In one aspect of the present disclosure, the feed stream is recovered from the production of acrylic acid by propylene oxidation, wherein said feed stream comprising acrylic acid, acetic acid, propionic acid, water, and high boiling by-products. For example, such processes are described in U.S. Pat. Nos. 4,031,135, 4,147,885, and 4,365,087 which are herein incorporated by reference.

In another aspect of the present disclosure, the feed stream is recovered from the production of acrylic acid from alternative or bio-based routes to acrylic acid such as propane oxidation, 3-hydroxypropionic acid, glycerol, and lactic acid where said feed stream comprising acrylic acid, acetic acid, propionic acid, water, and high boiling by-products. For example, such processes are described and referenced in U.S. Pat. No. 9,493,393 which is herein incorporated by reference.

One embodiment of the present disclosure is for the separation of acetic acid from acrylic acid from an intermediate acrylic acid product produced from the reaction of acetic acid and formaldehyde (an aldolization reaction). U.S. Pat. Nos. 8,765,629 and 8,883,672 describe reactions of acetic acid and formaldehyde suitable for use this disclosure and are herein incorporated by reference. The feed composition for these embodiments comprises acrylic acid less than 80 wt %, an acetic acid concentration greater than 1 wt %, and a propionic acid concentration of less than 1 wt %, and a maleic acid concentration less than 5 wt %.

Another embodiment of the present disclosure is for the separation of propionic acid from acrylic acid using an azeotropic dividing wall column with water as the entrainer. The acrylic acid can come from a variety of processes including, but not limited to propylene oxidation, the condensation of formaldehyde and acetic acid, and the production of bio-based acrylic acid from glycerol. The feed composition for one embodiment comprises acrylic acid greater than 10 wt % (in another embodiment, the acrylic acid concentration is greater than 20 wt %), and a propionic acid concentration of less than 5 wt % (in another embodiment, the propionic acid concentration is less than 1 wt %).

In general, acrylic acid has a strong tendency to polymerize, so in some embodiments a stabilizing polymerization inhibitor is added to the process. Any acrylic acid polymerization inhibitors are suitable for use in the present disclosure. For example, in some embodiments, any acrylic acid polymerization inhibitor that doesn't azeotrope with water is suitable for use in this process. In some embodiments, suitable polymerization inhibitors may form minimum boiling azeotropes with water. In these embodiments, the polymerization inhibitors should be fed into the column in a place where water concentration is very low, the acrylic acid concentration is fairly high, or the column temperature is high enough to enable acrylic acid polymerization. For example, in some embodiments, the polymerization inhibitors are fed into the column towards the bottom of the column or into the column reboiler. In one embodiment, the polymerization inhibitors are selected from diphenylamine or its derivatives, phenothiazine, p-methoxyphenol, hydroquinone or hydroquinone monomethylether, nitroso compounds such as 2-methyl-2-nitrosopropane, nitrosobenzene, and 4-nitrosophenol.

In some embodiments, the high boiling by-products, such as maleic acid and acrylic acid oligomers, are removed in the column's bottom outflow product stream. In some embodiments, an alternative configuration is to remove acetic acid from the column using an optional concentrated upper side stream located, in one embodiment, above the dividing wall in the wall-free column top zone where the acetic acid is at or near its most concentrated point in the column.

In some embodiments, wherein the product top stream from the azeotropic distillation column further comprises other organic compounds forming minimum boiling azeotropes with water such as furfural, benzaldehyde, and toluene. In one embodiment, the product top stream contains at least 90% of the propionic acid in the feed stream.

In some embodiments, the column pressure is set to control the column temperature where the concentration of acrylic acid is greater than 35 wt %. For example, in one embodiment the column temperature is less than 140° C.; in one embodiment, the column temperature is less than 130° C.; in one embodiment, the column temperature is less than 120° C.; and in another embodiment, the column temperature is less than 115° C. The column operation is also controlled in order to enable the separation of acrylic acid from acetic acid, with the acetic acid concentration in the acrylic acid main column side stream being controlled to less than 1500 ppm, or to less than 500 ppm, with the propionic acid concentration in the acrylic acid side stream being controlled to less than 500 ppm, or to less than 100 ppm. The column distillate (i.e. top) temperature will be set by the column pressure and will be a function of the distillate composition at that pressure. For example, in some embodiments, if the feed contains a large portion of acetic acid, the acetic acid may be the primary component in the distillate and the boiling point of acetic acid at that pressure will be a major influence in the column top temperature.

In some embodiments, the split of liquid from the top section to the two sides of the dividing wall and the split of the vapor from the bottom section to the two sides of the dividing wall have an impact on the reflux and boil-up ratios needed to achieve desired purity and recoveries. The lowest energy operation will correspond to a particular split of the liquid and vapor flows, and this split is different for different feed compositions, column staging, and purity and recovery requirements. In one embodiment of this disclosure, the split is defined as the % or mass fraction flowing to the feed side of the wall. In some embodiments, the liquid and vapor split ratios are close to each other, for best energy requirements.

There are several dividing wall column configurations suitable for use in the present disclosure. In some embodiments, suitable configurations are described in in U.S. Pat. No. 9,504,934 which is herein incorporated by reference. For example, one of these configurations is shown in FIG. 4, which provides improved energy efficiency when compared to a conventional distillation sequence, but this configuration has the advantage of only requiring liquid transfers instead of vapor and liquid transfers to the various sections as required by the configurations shown in FIGS. 2 and 3.

EXAMPLES

Aspen Plus V8.6 was used as the modeling software for all examples. An internally developed Vapor-Liquid Equilibria (VLE) package was used as a basis for all model results documented in this disclosure. Maleic acid was typically present in acrylic acid process streams. In these models, maleic acid also represents other high boiling components such as acrylic acid oligomers. The resulting VLE at P=760 mmHg is shown in the following Table 1.

TABLE 1

Physical Property Information (Mass Fraction) (P = 760 mmHg)

| Boiling Point (° C.) | Formaldehyde | Water | Acetic Acid | Propionic Acid | Acrylic Acid | Maleic Acid |
|---|---|---|---|---|---|---|
| −19.5 | 1.00 | | | | | |
| 99.8 | | 0.79 | | 0.21 | | |
| 100.0 | | 1.00 | | | | |
| 118.0 | | | 1.00 | | | |
| 140.2 | | | | 0.63 | 0.37 | |
| 140.9 | | | | 1.00 | | |
| 142.0 | | | | | 1.00 | |
| 292.2 | | | | | | 1.00 |

The dividing wall column structure was modeled in Aspen, using two RADFRAC column models, in a typical formulation for a thermally integrated column configuration with a pre-fractionator. The pre-fractionator column represents the feed side of the dividing wall, and has no reboiler or condenser. The second main column represents the top section, the draw side of the dividing wall, and the bottom section of the column. All of the vapor leaving the top of the pre-fractionator was fed to the main column just above the wall location, and all of the liquid leaving the bottom of the pre-fractionator was fed to the main column just below the wall location.

Example 1

This example represents an embodiment, without the optional side draw product stream for higher purity acetic acid.

TABLE 2

Summary of Key Input Parameters for Example 1

| Property | Pre-fractionator | Main Column |
|---|---|---|
| Top Pressure, torr | 125 | 100 |
| Bottom Pressure, torr | 175 | 200 |
| Feed Stage | 40 | — |
| Side-Draw | — | 40 |
| Top Column Stages | — | 25 |
| Pre-fractionator/Main Column Stages | 30 | 30 |
| Bottom Column Stages | — | 10 |
| Liquid split across dividing wall | 85% | 15% |
| Vapor split across dividing wall | 85% | 15% |
| Reflux Ratio | — | 3.7 |
| Distillate to Feed weight ratio | — | 0.75 |

TABLE 3

Results Summary for Example 1

| Stream | 210 | 230 | 240 | 250 |
|---|---|---|---|---|
| | Mass Fraction | | | |
| Water | 0.050 | 0.067 | trace | trace |
| Acetic Acid | 0.700 | 0.933 | 365 PPM | trace |
| Acrylic Acid | 0.200 | 629 PPM | 1.000 | 200 PPM |
| Propionic Acid | 10 PPM | trace | 51 PPM | trace |
| Maleic Acid | 0.050 | trace | trace | 1.000 |
| | Recovery (%) | | | |
| Water | — | 100.0% | 0.0% | 0.0% |
| Acetic Acid | — | 100.0% | 0.0% | 0.0% |
| Acrylic Acid | — | 0.2% | 99.8% | 0.0% |
| Propionic Acid | — | 0.0% | 100.0% | 0.0% |
| Maleic Acid | — | 0.0% | 0.0% | 100.0% |

Example 2

This example represents an embodiment, with the optional upper side draw product stream for higher purity acetic acid.

TABLE 4

Summary of Key Input Parameters for Example 2

| Property | Pre-fractionator | Main Column |
|---|---|---|
| Top Pressure, torr | 125 | 100 |
| Bottom Pressure, torr | 175 | 200 |
| Optional Conc. Acetic Acid Side-draw | — | 3 |
| Feed Stage | 40 | — |
| Side-Draw | — | 40 |
| Top Column Stages | — | 25 |
| Pre-fractionator/Main Column Stages | 30 | 30 |
| Bottom Column Stages | — | 10 |
| Liquid split across dividing wall | 87% | 13% |
| Vapor split across dividing wall | 87% | 13% |
| Reflux Ratio | — | 26 |
| Conc. Acetic Acid Side-draw to feed weight ratio | — | 0.60 |
| Distillate to Feed weight ratio | — | 0.15 |

TABLE 5

Summary for Example 2

| Stream | 210 | 230 | 220 | 240 | 250 |
|---|---|---|---|---|---|
| | Mass Fraction | | | | |
| Water | 0.050 | 0.130 | 0.051 | trace | trace |
| Acetic Acid | 0.700 | 0.870 | 0.949 | 7 PPM | trace |
| Acrylic Acid | 0.200 | 271 PPM | 619 PPM | 1.000 | 200 PPM |
| Propionic Acid | 10 PPM | trace | trace | 50 PPM | trace |
| Maleic Acid | 0.050 | trace | trace | trace | 1.000 |
| | Recovery (%) | | | | |
| Water | — | 39.1% | 60.9% | 0.0% | 0.0% |
| Acetic Acid | — | 18.7% | 81.3% | 0.0% | 0.0% |
| Acrylic Acid | — | 0.0% | 0.2% | 99.8% | 0.0% |
| Propionic Acid | — | 0.0% | 0.0% | 100.0% | 0.0% |
| Maleic Acid | — | 0.0% | 0.0% | 0.0% | 100.0% |

Example 3

This example represents an embodiment, without the additional side draw product stream for higher purity acetic acid. The feed to this column has a much higher percentage of acrylic acid than the feed for examples 1 and 2, and much less acetic acid.

TABLE 6

Summary of Key Input Parameters for Example 3

| Property | Pre-fractionator | Main Column |
|---|---|---|
| Top Pressure, torr | 125 | 100 |
| Bottom Pressure, torr | 175 | 200 |
| Feed Stage | 40 | — |
| Side-Draw | — | 40 |
| Top Column Stages | — | 25 |
| Pre-fractionator/Main Column Stages | 30 | 30 |
| Bottom Column Stages | — | 10 |
| Liquid split across dividing wall | 59% | 41% |
| Vapor split across dividing wall | 59% | 41% |
| Reflux Ratio | — | 9.5 |
| Distillate to Feed weight ratio | — | 0.21 |

TABLE 7

Summary for Example 3

| Stream | 210 | 230 | 240 | 250 |
|---|---|---|---|---|
| | Mass Fraction | | | |
| Water | 0.040 | 0.190 | trace | trace |
| Acetic Acid | 0.170 | 0.808 | 421 PPM | trace |
| Acrylic Acid | 0.750 | 0.002 | 1.000 | 250 PPM |
| Propionic Acid | 10 PPM | trace | 13 PPM | trace |
| Maleic Acid | 0.040 | trace | trace | 1.000 |
| | Recovery (%) | | | |
| Water | — | 100.0% | 0.0% | 0.0% |
| Acetic Acid | — | 99.8% | 0.2% | 0.0% |
| Acrylic Acid | — | 0.0% | 100.0% | 0.0% |
| Propionic Acid | — | 0.0% | 100.0% | 0.0% |
| Maleic Acid | — | 0.0% | 0.0% | 100.0% |

Example 4

This example represents an embodiment, where water was used as an entrainer and azeotroping agent to remove impurities from the acrylic acid.

TABLE 8

Summary of Key Input Parameters for Example 4

| Property | Pre-fractionator | Main Column |
|---|---|---|
| Top Pressure, torr | 125 | 100 |
| Bottom Pressure, torr | 175 | 200 |
| Water Entrainer | — | 22 |
| Feed Stage | 28 | — |
| Water to Feed Weight Ratio | 2.0 | — |
| Side-Draw | — | 53 |
| Top Column Stages | — | 25 |
| Pre-fractionator/Main Column Stages | 30 | 30 |
| Bottom Column Stages | — | 10 |
| Liquid split across dividing wall | 57% | 43% |
| Vapor split across dividing wall | 57% | 43% |
| Reflux Ratio | — | 9.5 |
| Distillate to Feed weight ratio | — | 2.0 |

TABLE 9

Summary for Example 4

| Stream | 310 | 315 | 330 | 340 | 350 |
|---|---|---|---|---|---|
| | Mass Fraction | | | | |
| Water | 0.005 | 1.000 | 0.990 | trace | trace |
| Acetic Acid | 0.005 | — | 0.002 | trace | trace |
| Acrylic Acid | 0.800 | — | 0.005 | 1.000 | trace |
| Propionic Acid | 0.005 | — | 0.002 | 99 PPM | trace |
| Maleic Acid | 0.185 | — | trace | trace | 1.000 |
| | Recovery (%) | | | | |
| Water | — | — | 100.0% | 0.0% | 0.0% |
| Acetic Acid | — | — | 100.0% | 0.0% | 0.0% |
| Acrylic Acid | — | — | 1.3% | 98.7% | 0.0% |
| Propionic Acid | — | — | 98.5% | 1.6% | 0.0% |
| Maleic Acid | — | — | 0.0% | 0.0% | 100.0% |

Example 1 and Example 2 do not include water as an entrainer, and illustrate the production of high purity acrylic acid starting from a feed stream with high acetic acid concentration (70 wt %) and low acrylic acid concentration (20 wt %) and the final product of the acrylic acid in the side draw stream has less than 500 ppm of acetic acid.

Example 3 does not include water as an entrainer, and illustrates the production of high purity acrylic acid starting from a feed stream with high acrylic acid concentration (75% wt) and low acetic acid concentration (17 wt %) and the final product of acrylic acid in the side draw stream has less than 500 ppm acetic acid.

Example 4 illustrates the use of water as an entrainer for the production of high purity acrylic acid starting from a feed stream with high acrylic acid concentration (80 wt %), low acetic acid concentration (0.5 wt %), and low propionic acid concentration (0.5 wt %) and the final product of acrylic acid in the side draw stream has less than 500 ppm acetic acid and less than 100 ppm propionic acid.

We claim:

1. A process for purifying acrylic acid from a feed stream composition comprising water, acrylic acid, acetic acid, and propionic acid using a dividing wall column, the process comprising:
   supplying the feed stream into the dividing wall column operated at a temperature and pressure such that the feed stream is separated into at least a product top stream, a product bottom stream, and a product side stream and optionally a concentrated product upper side stream; and wherein the feed stream and the product side stream are located on opposite sides of the column and are separated by the dividing wall and wherein the dividing wall extends vertically through the column from a dividing wall-free column top zone to a dividing wall-free column bottom zone; and adding entraining water as an entrainer and azeotroping agent, into the dividing wall-free column top zone in the column; and wherein the entraining water to feed ratio (wt/wt) in the column is greater than 1.0; and wherein the product top stream comprises water, acetic acid, propionic acid and low boiling by-products, the product bottom stream comprises high-boiling by-products, and the product side stream comprises acrylic acid and the optional concentrated product upper side stream is located near the top of the column and comprises a concentrated acid side-stream comprising acetic acid, and wherein the optional concentrated product upper side stream is located above the dividing wall in the wall-free column top zone.

2. A process for purifying acrylic acid from a feed stream composition comprising water, acrylic acid, acetic acid, and propionic acid using a dividing wall column, the process comprising:

supplying the feed stream into the dividing wall column operated at a temperature and pressure such that the feed stream separated into: two product top streams, one on each side of the column; two product bottom streams, one on each side of the column; a product stream on the side of the column wall opposite the feed stream; and optionally two concentrated product upper side streams, one on either side of the column; and wherein the feed stream and the product stream on the side of the column wall opposite the feed stream are located on opposite sides of the column and are completely separated by the dividing wall and wherein the dividing wall extends vertically through the entire column from the top of the column to the bottom of the column; and adding entraining water as an entrainer and azeotroping agent, near the top of the column wherein the entrainer is fed on each side of the column; and wherein the entraining water to feed ratio (wt/wt) in the column is greater than 1.0; and wherein the product top streams comprise water, acetic acid, propionic acid and low boiling by-products, the product bottom streams comprise high boiling by-products, and the product stream on the side of the column wall opposite the feed stream comprises acrylic acid and the optional concentrated product upper side streams are located near the top of the column and comprise concentrated acid side-streams comprising acetic acid.

3. A process according to claim 1, wherein the feed stream comprises 1-80 wt % acrylic acid, up to 80 wt % acetic acid, and up to 60 wt % additional components where the total composition does not exceed 100 wt % and wherein the product side stream is high purity acrylic acid with less than 500 ppm acetic acid.

4. A process according to claim 1, wherein the feed stream comprises 5-50 wt % acrylic acid, 50-80 wt % acetic acid, 1-20 wt % water, and 0.5-1 wt % propionic acid or wherein the feed stream comprises 50-80 wt % acrylic acid, 0.1-20 wt % acetic acid, 0.1-10 wt % water, and 0.001-0.5 wt % propionic acid and wherein the product side stream is high purity acrylic acid with less than 500 ppm acetic acid and less than 100 ppm propionic acid.

5. A process according to claim 1, wherein greater than 80 wt % of the acrylic acid in the feed stream is recovered in the product side stream.

6. A process according to claim 1, wherein the feed stream is recovered from the production of acrylic acid by propylene oxidation, said feed stream comprising acrylic acid, acetic acid, propionic acid, water, and heavy by-products.

7. A process according to claim 1, wherein the feed stream is recovered from the production of acrylic acid by an aldolization reaction, said feed stream comprising acrylic acid, acetic acid, propionic acid, water, and heavy by-products.

8. A process according to claim 1, wherein the feed stream is recovered from the production of acrylic acid from propane oxidation or bio-based processes which comprise the use of 3-hydroxypropionic acid, glycerol, or lactic acid as starting materials/reactants, said feed stream comprising acrylic acid, acetic acid, propionic acid, water, and high boiling by-products.

9. A process according to claim 1 or 2, wherein the product top stream(s) further comprises other organic compounds forming minimum boiling azeotropes with water.

10. A process according to claim 1 or 2, wherein the product top stream(s) contains at least 90 wt % of the propionic acid in the feed stream.

11. A process according to claim 1, wherein the acrylic acid in the product side stream is in a higher concentration than in the feed stream.

12. A process according to claim 1, wherein the column operates at a pressure less than or equal to 1000 torr.

13. A process according to claim 1, wherein the column temperature is controlled to less than 140° C. when the concentration of acrylic acid is greater than 35 wt % in the column.

14. A process according to claim 1, wherein the column temperature is controlled to less than 115° C. when the concentration of acrylic acid is greater than 35 wt % in the column.

15. A process according to any one of claim 1 or 2 wherein the water to feed ratio (wt/wt) in the column is greater than 1.4.

16. A process according to claim 1, wherein the feed stream comprises less than 80 wt % acrylic acid.

* * * * *